United States Patent

Lee et al.

[11] Patent Number: 5,994,556
[45] Date of Patent: Nov. 30, 1999

[54] BIS(ORTHO-DIARYLPHOSPHINOPHENYL)-TETRAHYDRO-BI(1,3-OXAZOLE) AND A PREPARATION METHOD THEREOF

[75] Inventors: Sang-Gi Lee; Choong-Eui Song; Chung-Woo Lim, all of Seoul, Rep. of Korea

[73] Assignee: Korea Institute of Science and Technology, Seoul, Rep. of Korea

[21] Appl. No.: 09/208,163

[22] Filed: Dec. 9, 1998

[30] Foreign Application Priority Data

Dec. 31, 1997 [KR] Rep. of Korea ............... 97/80691

[51] Int. Cl.⁶ ............... C07D 263/08; C07D 263/10; C07D 413/04
[52] U.S. Cl. ............... 548/237
[58] Field of Search ............... 548/237

[56] References Cited

FOREIGN PATENT DOCUMENTS 4-266887  9/1992  Japan ............... C07D 413/14

OTHER PUBLICATIONS

SYNLETT (Apr. 1991, pp. 257–259) C2–Symmetric Bioxazolines and Bithiazolines as New Chiral Ligands for Metal Icon Catalyzed Asymmetric Syntheses: Asymmetric Hydrosilylation.

Otganometallics (1991), 10, 500–508.

Journal of Organometallic Chemistry, (1988) pp. 413–424.

Tetrahedron: Asymmetry, vol. 8 No. 17, pp. 2927–2932, (1997).

Organometallics (1989), 5, pp. 846–848.

Tetrahedron: Asymmetry, vol. 6. No. 3, pp. 653–656, (1995).

*Primary Examiner*—Joseph K. McKane
*Assistant Examiner*—Jane C. Oswecki
*Attorney, Agent, or Firm*—Darby & Darby

[57] ABSTRACT

The present invention relates to optically pure bis(o-diarylphosphinophenyl)-tetrahydro-bi(1,3-oxazole) compounds represented by the formula (I) and a preparation method thereof. Bis(o-diarylphosphinophenyl)-tetrahydro-bi(1,3-oxazole) compounds of the present invention include (4S,4'S)-2,2'-bis(o-diarylphosphinophenyl)-4,4',5,5'-tetrahydro-4,4'-bi(1,3-oxazole) represented by the formula (Ia) and its enantiomer, (4R,4'R)-2,2'-bis(o-diarylphosphinophenyl)-4,4',5,5'-tetrahydro-4,4'-bi(1,3-oxazole) represented by the formula. The compounds of the present invention can be utilized in asymmetric hydrosilylation, hydrogenation, cyclopropylation and alkylation reactions.

14 Claims, No Drawings

BIS(ORTHO-DIARYLPHOSPHINOPHENYL)-TETRAHYDRO-BI(1,3-OXAZOLE) AND A PREPARATION METHOD THEREOF

BACKGROUND OF THE INVENTION

The present invention relates to optically pure bis(o-diarylphosphinophenyl)-tetrahydro-bi(1,3-oxazole) compounds represented by the formula (I) and a preparation method thereof. Bis(o-diarylphosphinophenyl)-tetrahydro-bi(1,3-oxazole) compounds of the present invention include (4S,4'S)-2,2'-bis(o-diarylphosphinophenyl)-4,4',5,5'-tetrahydro-4,4'-bi(1,3-oxazole) as represented by the formula (Ia) and its optical isomer, (4R,4'R)-2,2'-bis(o-diarylphosphinophenyl)-4,4',5,5'-tetrahydro-4,4'-bi(1,3-oxazole) as represented by the formula (Ib) depending on the absolute ratio of the initial reactant, tartaric acid.

Generally, optically pure compounds are increasingly demanded recently since the optical isomers have different biological properties. Therefore, preparation methods for the optically pure compounds are required greatly. Especially, the asymmetric hydrosilylation, hydrogenation, cyclopropylation, alkylation using the metallic catalysts such as Rh, Ru, Ir, Co, Cu and Pd are used in preparing the optically pure compounds. Therefore, development of an effective ligand for these reactions is absolutely necessary in developing the medicines, pesticides, food additives and fragrances. To date, the most widely developed chiral ligands for the asymmetric catalytic reaction are phosphine and oxazoline compounds that contain phosphorus and nitrogen, respectively. Some of the chiral compounds of the previous art, however, have a room for improvement. For instance, the bisphosphine chiral ligand for the hydrosilylation of ketones by using the metallic Rh(I) such as 2,3-o-isopropyliden-2,3-dihydroxy-1,4-bis(diphenylphosphinobutane (DIOP) was used to obtain the product with only 60% of optical purity (Organometallics, 1991, 10, 500). Another study shows that the product with an average of more than 90% optical purity was obtained by using an optically pure bis(oxazolyl)pyridine ligand with, however, a shortcoming that more than 4 to 10 equivalent weights of the excess ligand had to be used for the reaction (Organometallics, 1989, 8, 846; J. Organomet. Chem. 1988, 346, 413).

SUMMARY OF THE INVENTION

The present invention relates to optically pure bis(o-diarylphosphinophenyl)-tetrahydro-bi(1,3-oxazole) compounds represented by the formula (I) and a preparation method thereof.

DETAILED DESCRIPTION OF THE INVENTION

The present invention relates to optically pure bis(o-diarylphosphinophenyl)-tetrahydro-bi(1,3-oxazole) compounds represented by the formula (I) and a preparation method thereof. Bis(o-diarylphosphinophenyl)-tetrahydro-bi(1,3-oxazole) compounds of the present invention include (4S,4'S)-2,2'-bis(o-diarylphosphinophenyl)-4,4',5,5'-tetrahydro-4,4'-bi(1,3-oxazole)represented by the formula (Ia) and its optical isomer, (4R,4'R)-2,2'-bis(o-diarylphosphinophenyl)-4,4',5,5'-tetrahydro-4,4'-bi(1,3-oxazole) represented by the formula (Ib) depending on the absolute configuration of the initial reactant, tartaric acid.

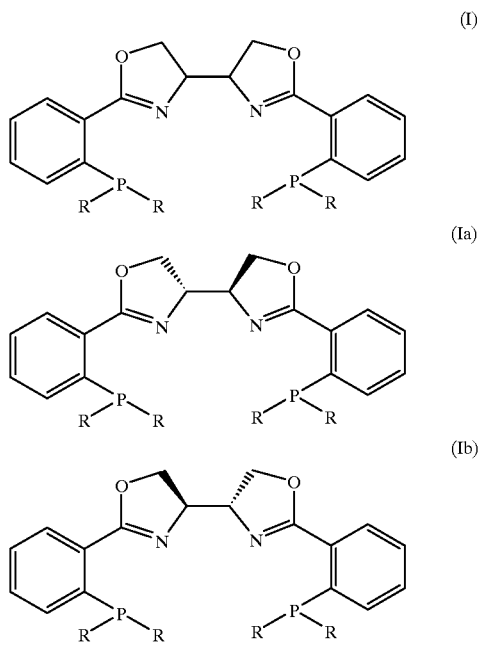

wherein, R represents an aromatic ring such as phenyl or naphthyl.

In the present invention, a novel chiral ligand which contains phosphine and oxazoline simultaneously in one compound was developed to overcome the shortcomings of the separate use of phosphine or oxazoline ligands of the previous art.

Briefly, bis(o-diarylphosphinophenyl)-tetrahydro-bi(1,3-oxazole) compounds represented by the formula (I) can be prepared by the 'Method 1' by reacting (S)-bis(o-dihalophenyl)-tetrahydro-bi(1,3-oxazole) of the formula (II) or its enantiomer (R)-bis(o-dihalophenyl)-tetrahydro-bi(1,3-oxazole) of the formula (III) with alkali metal diarylphosphide of the formula (IV). Bis(o-diarylphosphinophenyl)-tetrahydro-bi(1,3-oxazole) compounds represent by the formula (I) can also be prepared by the 'Method 2' by reacting (S)-diphenyl tetrahydro-bi-(1,3-oxazole) of the formula (V) or its enantiomer (R)-diphenyl tetrahydro-bi-(1,3-oxazole) of the formula (VI) with monohalo diarylphosphine of the formula (VII) and alkyl lithium of the formula (VIII).

The detailed preparation methods in preparing bis(o-diarylphosphinophenyl)-tetrahydro-bi(1,3-oxazole) compounds represented by the formula (I) are as follows. In the "Method 1', the reactant, (S)-bis(o-dihalophenyl)-tetrahydro-bi(1,3-oxazole) of the formula (II) or its enantiomer (R)-bis(o-dihalophenyl)-tetrahydro-bi(1,3-oxazole) of the formula (III) can be prepared easily by following the procedure in the literature [Lee, S. Gi; Lim, C. W.; Song, Choong Eui; Kim, In-O, Tetrahedron:Asymmetry 1997, 8, 2979, Korean Patent (Application Number 97-37237)]. Bis (o-diarylphosphinophenyl)-tetrahydro-bi(1,3-oxazole) compounds represented by the formula (I) is prepared by reacting (S)-bis(o-dihalophenyl)-tetrahydro-bi(1,3-oxazole) of the formula (II) or its enantiomer (R)-bis(o-dihalophenyl)-tetrahydro-bi(1,3-oxazole) of the formula (III) with alkali metal diarylphosphide of the formula (IV) by using diethyl ether, dioxane, benzene or toluene as a solvent at 20~100° C. for ca. 30 min to 2 hours.

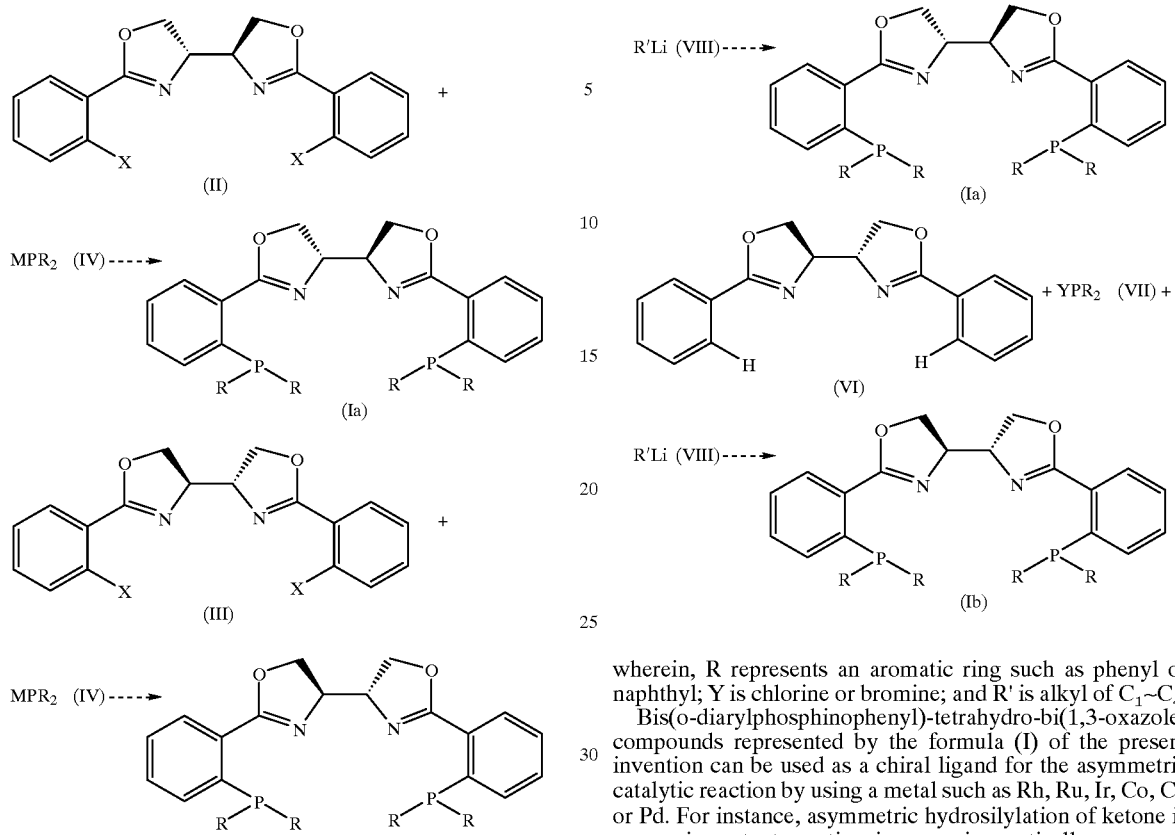

wherein, X represents fluorine, chlorine, bromine or iodine; R is an aromatic ring such as phenyl or naphthyl; and M is an alkali metal such as lithium, sodium or potassium.

In the "Method 2', (S)-diphenyl tetrahydro-bi(1,3-oxazole) of the formula (V) or its enantiomer (R)-diphenyl tetrahydro-bi(1,3-oxazole) of the formula (VI) can be prepared by following the procedure in the literature as in the 'Method 1' by using L-tartaric acid or D-tartaric acid, respectively. In detail, after reacting (S)-diphenyl tetrahydro-bi(1,3-oxazole) of the formula (V) or its enantiomer (R)-diphenyl tetrahydro-bi(1,3-oxazole) of the formula (VI) with alkyl lithium of the formula VIII in tetrahydrofuran or diethyl ether as a solvent at −78~0° C. for ca. 1 to 3 hours, mono halo diarylphosphine of the formula (VII) is added to the mixture and reacted at 20~80° C. for ca. 1 to 6 hours to prepare bis(o-diarylphosphinophenyl)-tetrahydro-bi(1,3-oxazole) compounds represented by the formula (I).

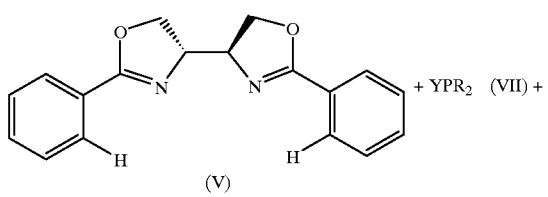

wherein, R represents an aromatic ring such as phenyl or naphthyl; Y is chlorine or bromine; and R' is alkyl of $C_1$~$C_4$.

Bis(o-diarylphosphinophenyl)-tetrahydro-bi(1,3-oxazole) compounds represented by the formula (I) of the present invention can be used as a chiral ligand for the asymmetric catalytic reaction by using a metal such as Rh, Ru, Ir, Co, Cu or Pd. For instance, asymmetric hydrosilylation of ketone is a very important reaction in preparing optically pure secondary alcohols. Therefore we have examined the efficiency of (4S,4'S)-2,2'-bis(o-diarylphosphinophenyl)-4,4',5,5'-tetrahydro-4,4'-bi(1,3-oxazole) represented by the formula (Ia) and its opticalisomer,(4R,4'R)-2,2'-bis(o-diarylphosphinophenyl)-4,4',5,5'-tetrahydro-4,4'-bi(1,3-oxazole) represented by the formula (Ib) as a ligand in the asymmetric hydrosilylation of acetophenone using metallic Ru as a catalyst. In detail, a mixture containing 0.005 mmol of bis(o-diarylphosphinophenyl)-tetrahydro-bi(1,3-oxazole) represented by the formula (I), 0.0025 mmol of [Rh(COD)Cl]$_2$ and 1 mmol of acetophenone was stirred for an hour at room temperatures, and 1.5 mmol of diphenyl silane was added to the mixture at −10~0° C. After the reaction mixtures was stirred at 0° C. for 3~5 hours, reaction was terminated by adding methanol and 0.1 N HCl aqueous solution. After extracting the organic layer with diethyl ether, a product (R)-1-phenylethyl alcohol with a very high optical purity (97%) and high yield (98%) was obtained by using a column chromatography with a silica column. When compared with the asymmetric hydrosilylation reactions using the oxazole or phosphine ligands in the previous art [Organometallics, 1991, 10, 508; Synlett 1991, 257; Organometallics, 1989, 8, 846, *J. Prganomet. Chem.*, 1988, 3496, 413], secondary alcohol with the highest optical purity can be obtained in ca. 3~5 hours by using very small quantities of ligand in the present invention whereas it takes ca. 24 hours in the previous art.

The invention will be further illustrated by the following examples, but not limited to the examples given.

EXAMPLE 1

(4S,4'S)-2,2'-bis(o-diarylphosphinophenyl)-4,4',5,5'-tetrahydro-4,4'-bi(, 1,3-oxazole)

Difluorobioxazole [formula (II): X=F] (0.5 g) dissolved in 3 ml of anhydrous tetrahydrofuran was added to a 6 ml of 0.5

M potassium diphenylphosphide [formula (IV): M=potassium, R=phenyl] tetrahydrofuran solution at room temperatures. After the reaction mixture was refluxed under heat for 30 min while stirring, 5 ml of water and 10 ml of dichloromethane were added. After the organic layer was separated, the aqueous layer was extracted 3 times with 10 ml of dichloromethane. After the organic layer was dried with magnesium sulfate, and the solvent was evaporated by distillation under reduced pressure, the remainder was purified by using a silica column chromatography. The product [formula (Ia), R=phenyl] was obtained with a 70% yield.

$[a]_D^{24}$:+53.2 (c0.5, $CHCl_3$)

melting point: 132~133° C.

1H-NMR (300 MHz: $CDCl_3$) d: 7.87 (m, 2H). 7.38–7.20 (m, 24H), 6.89 (m, 2H), 4.22 (m, 2H), 3.57 (pseudo d, J=8.2 Hz, 4H)

31P-NMR (121 MHz, $CDCL_3$) d: 11.62

HRMS (FAB) calculated value of $C_{32}H_{35}N_2O_2P_2$[(M+H)+]: 661.2173, experimental value: 661.2170

EXAMPLE 2

(4R,4'R)-2,2'-bis(o-diarylphosphinophenyl)-4,4',5,5'-tetrahydro-4,4'-bi(1,3-oxazole)

Difluorobioxazole [formula (III): X=F] (0.5 g) dissolved in 3 ml of anhydrous tetrahydrofuran was added to 6 ml of 0.5 M potassium diphenylphosphide [formula (IV): M=potassium, R=phenyl] tetrahydrofuran solution at room temperatures. After the reaction mixture was refluxed under heat for 30 min while stirring, 5 ml of water and 10 ml of dichloromethane were added. After the organic layer was separated, the aqueous layer was extracted 3 times with 10 ml of dichloromethane. After the organic layer was dried with magnesium sulfate, and the solvent was evaporated by distillation under reduced pressure, the remainder was purified by using a silica column chromatography. The product [formula (Ib), R=phenyl] was obtained with a 74% yield.

$[a]_D^{24}$:−52.9 (c0.5, $CHCl_3$)

melting point: 129~131° C.

1H-NMR (300 MHz: $CDCl_3$) d: 7.87 (m, 2H). 7.38–7.20 (m, 24H), 6.89 (m, 2H), 4.22 (m, 2H), 3.57 (pseudo d, J=8.2 Hz, 4H)

31P-NMR (121 MHz, $CDCL_3$) d: 11.62

HRMS (FAB) calculated value of $C_{32}H_{35}N_2O_2P_2$[(M+H)+]: 661.2173, experimental value: 661.2170

EXAMPLE 3

Asymmetric hydrosilylation of ketones using bis(o-diarylphosphinophenyl)-tetrahydro-bi(1,3-oxazole) as a ligand After dissolving a mixed solution of 0.25 mmol of [Rh(COD)Cl]$_2$, 0.0005 mmolof(4S,4'S)-2,2'-bis(o-diarylphosphinophenyl)-4,4, 5,5'-tetrahydro-4,4'-bi(1,3-oxazole) prepared in Example 1 and 1 mmol acetophenone in 1 ml of tetrahydrofuran, the solution was stirred for an hour at room temperatures. At 0 ° C., 1 mmol of acetophenone and 1.5 mmol of diphenylsilane were added to the mixture. After the reaction mixture was stirred for 7 hours at 0° C., 5 ml of methanol and 10 ml of 0.1 N HCl aqueous solution were added. After the organic layer was extracted with diethyl ether and dried (Na2SO4), solvent was removed by vacuum distillation. The remainder was purified by using a silica column chromatography to obtain an optically active secondary alcohol, (R)-1-phenyl ethyl alcohol.

yield: 98% optical purity 97% ee.

According to the present invention, an optically pure novel compound, bis(o-diarylphosphinophenyl)-tetrahydro-bi(1,3-oxazole) represented by the formula I was prepared, which can be utilized in asymmetric hydrosilylation, hydrogenation, cyclopropylation and alkylation reactions.

What is claimed is:

1. Bis(o-diarylphosphinohenyl)-tetrahydro-bi(1,3-oxazole)derivatives represented by the formula (I)

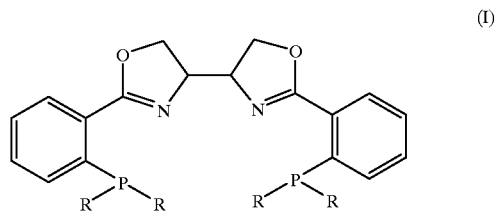

(I)

wherein, R represents an aromatic ring selected from the group consisting of phenyl or naphthyl.

2. The optical isomers of the derivatives according to claim 1 which is (4S,4'S)-2,2'-bis(o-diarylphosphinophenyl)-4,4',5,5'-tetrahydro-4,4'-bi(1,3-oxazole) represented by the formula (Ia) or (4R,4'R)-2,2'-bis(o-diarylphosphinophenyl)-4,4',5,5'-tetrahydro-4,4'-bi(1,3-oxazole) represented by the formula (Ib)

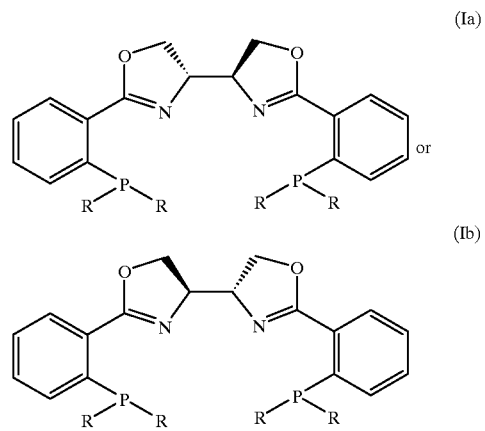

(Ia)

or (Ib)

wherein, R represents an aromatic ring selected from the group consisting of phenyl or naphythyl.

3. A method of preparing (4S,4'S)-2,2'-bis(o-diarylphosphinophenyl)-4,4',5,5'-tetrahydro-4,4'-bi(1,3-oxazole) represented by the formula (Ia) as defined in claim 2, which method comprises reacting (S)-bis(o-dihalophenyl)-tetrahydro-bi(1,3-oxazole) of the formula (II)

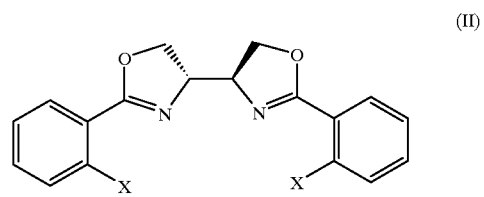

(II)

wherein X is fluorine, chlorine, bromine or iodine; and an alkali metal diarylphosphide (MPR$_2$), wherein M is an alkali metal selected from the group consisting of lithium, sodium or potassium, and wherein R$_2$ is diaryl; in the presence of a solvent.

4. A method of preparing (4R,4'R)-2,2'-bis(o-diarylphosphinophenyl)-4,4'5,5'-tetrahydro-4,4'-bi(1,3-oxazole) represented by the formula (Ib) as defined in claim 2, which method comprises reacting (R)-bis-o-dihalophenyl)-tetrahydro-bi(1,3-oxazole) of the formula (III)

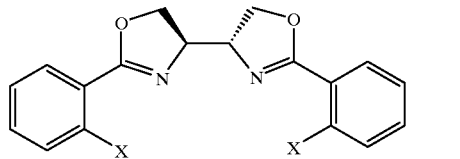

(III)

wherein X is fluorine, chlorine, bromine or iodine; and alkali metal diarylphosphide ($MPR_2$), wherein M is an alkali metal selected from the group consisting of lithium, sodium or potassium and wherein $R_2$ is diaryl; in the presence of a solvent.

5. A method of preparing (4S,4'S)-2,2'-bis(o-diarylphosphinophenyl)-4,4',5,5'-tetrahydro-4,4'-bi(1,3-oxazole) represented by the formula (Ia) as defined in claim 2, which method comprises reacting (S)-diphenyl tetrahydro-bi(1,3-oxazole) of the formula V,

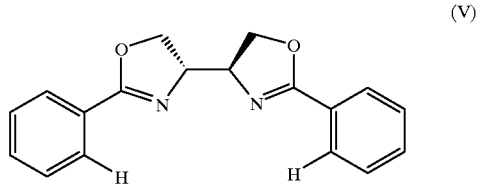

(V)

mono halo diarylphosphine ($YPR_2$), wherein Y is chlorine or bromine, and $R_2$ is diaryl; and alkyl lithium (R'Li), wherein R' is an alkyl of $C_1$~$C_4$; in the presence of solvent.

6. A method of preparing (4R,4'R)-2,2'-bis(o-diarylphosphinophenyl)-4,4',5,5'-tetrahydro-4,4'-bi(1,3-oxazole) represented by the formula (Ib) as defined in claim 2, which method comprises reacting (R)-diphenyl tetrahydro-bi(1,3-oxazole) of the formula VI,

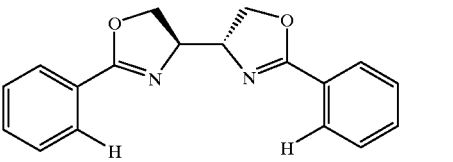

(VI)

mono halo diarylphosphine (YPR2), wherein Y is chlorine or bromine, and R2 is diaryl; and alkyl lithium (R'Li), wherein R' is an alkyl of $C_1$~$C_4$; in the presence of a solvent.

7. The method according to claim 3, wherein the solvent is selected from the group consisting of tetrahydrofuran, ethyl ether, dioxane, benezene and tolune.

8. The method according to claim 3, wherein the reaction is performed at 20~110° C. for 30 min~2 hours.

9. The method according to claim 4, wherein the solvent is selected from the group consisting of tetrahydrofuran, ethyl ether, dioxane, benzene and toluene.

10. The method according to claim 4, wherein the reaction is performed at 20~110° C. for 30 min~2 hours.

11. The method according to claim 5, wherein the solvent is tetrahydrofuran or ethyl ether.

12. The method according to claim 5, wherein the reaction is performed at 20~80° C. for 1~6 hours.

13. The method according to claim 6, wherein the solvent is tetrahydrofuran or ethyl ether.

14. The method according to claim 6, wherein the reaction is performed at 20~80° C. for 1~6 hours.

* * * * *